(12) United States Patent
Park

(10) Patent No.: US 10,292,780 B2
(45) Date of Patent: May 21, 2019

(54) HAPTIC GLOVES AND SURGICAL ROBOT SYSTEMS

(71) Applicant: Samsung Electronics Co., Ltd., Suwon-si, Gyeonggi-Do (KR)

(72) Inventor: Ki Cheol Park, Hwaseong-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 895 days.

(21) Appl. No.: 14/100,294

(22) Filed: Dec. 9, 2013

(65) Prior Publication Data

US 2014/0336669 A1 Nov. 13, 2014

(30) Foreign Application Priority Data

May 8, 2013 (KR) .................. 10-2013-0052173

(51) Int. Cl.
*A61B 34/30* (2016.01)
*A61B 34/00* (2016.01)

(52) U.S. Cl.
CPC .............. *A61B 34/76* (2016.02); *A61B 34/30* (2016.02); *A61B 2034/741* (2016.02)

(58) Field of Classification Search
CPC ......... A61B 34/30; A61B 34/37; A61B 34/76; A61B 34/35; A61B 2090/064; A61B 2090/065; A61B 2090/066; A61B 90/361; A61B 90/36; A61B 2034/305; A61B 2034/741; A61B 5/6806; A61B 17/00234; A61B 1/3132; A61B 2562/0247; A61B 2562/043; A61B 5/7455; G06F 3/016; G06F 3/14; G06F 3/033; B25J 13/025; B25J 13/02; B25J 13/084; B25J 9/1612;
(Continued)

(56) References Cited

U.S. PATENT DOCUMENTS 6,275,213 B1 * 8/2001 Tremblay ................ G06F 3/011
345/156
6,979,164 B2 * 12/2005 Kramer .................... G06F 3/011
340/407.1
(Continued)

FOREIGN PATENT DOCUMENTS

KR 20100065074 A 6/2010
KR 20100126154 A 12/2010
KR 20110099362 A 9/2011

*Primary Examiner* — Diane D Yabut
*Assistant Examiner* — Socrates L Boutsikaris
(74) *Attorney, Agent, or Firm* — Harness, Dickey & Pierce, P.L.C.

(57) ABSTRACT

A haptic glove configured to transmit haptic feedback to an operator of a surgical robot system may include: a plurality of vibrators on a first surface of the haptic glove, the plurality of vibrators configured to apply vibrations; at least one pressure sensor at a finger part of a second surface of the haptic glove opposite to the first surface, the at least one pressure sensor configured to sense grip force in the finger part; at least one sensation applier on the second surface, the at least one sensation applier configured to apply sensations including vibration or force to the finger part; and/or a controller configured to output the grip force sensed by the at least one pressure sensor, and configured to control the vibrations applied by the plurality of vibrators and the sensations applied by the at least one sensation applier.

19 Claims, 9 Drawing Sheets

(58) Field of Classification Search
CPC ........ A61F 2002/704; A61F 2002/5061; A61F 2002/6827; G05B 2219/40134
USPC ........................................................ 606/130
See application file for complete search history.

(56) References Cited

U.S. PATENT DOCUMENTS

2007/0021738 A1\* 1/2007 Hasser ................. A61B 8/4218
  606/1
2007/0164878 A1\* 7/2007 Baier ..................... G06F 3/014
  341/20
2009/0248037 A1\* 10/2009 Prisco .................... A61B 34/71
  606/130

\* cited by examiner

HAPTIC GLOVES AND SURGICAL ROBOT SYSTEMS

CROSS-REFERENCE TO RELATED APPLICATION(S)

This application claims priority from Korean Patent Application No. 10-2013-0052173, filed on May 8, 2013, in the Korean Intellectual Property Office (KIPO), the entire contents of which are incorporated herein by reference.

BACKGROUND

1. Field

Some example embodiments of the present disclosure may relate to surgical robot systems for controlling surgical robots by sensing motion of hands of operators.

2. Description of Related Art

A minimal invasive surgery generally represents surgeries in which the size of an affected part is minimal. The minimal invasive surgery, different from an open surgery having some portion of a body part of a human (for example, an abdomen) entirely open to perform a surgery, makes at least one incision (or invasive hole) in a size of between about 0.5 cm and about 1.5 cm, and an endoscope and various surgical tools are inserted through the incision such that a surgery is performed while observing an internal image of the abdomen.

The minimal invasive surgery involves less post-surgical pain while enabling an early recovery of intestinal movement and of the ability to ingest food earlier relative to the open surgery. In addition, the minimal invasive surgery requires shorter length of hospitalization, and thereby a return to a normal condition is faster. Furthermore, since an area of an incision from the minimal invasive surgery is small, an aesthetic effect is superior. Thus, the minimal invasive surgery is being applied in numerous types of surgeries, including gall bladder removal surgery, prostate cancer surgery, hernia correction surgery, etc., and is increasingly being used in the medical field.

In general, a surgery robot used in the minimal invasive surgery includes a master device and a slave device. The master device generates a control signal according to manipulation of a surgeon, and transmits the generated control signal to the slave device, and the slave device receives the control signal from the master device to perform a manipulation that is required for a surgery on a patient. The master device and the slave device may be incorporated into a single device, or may be separately provided from each other and disposed in a surgery room to perform a surgery.

The slave device is provided with at least one robot arm, and a surgical instrument is mounted at the end portion of each robot arm, and a surgical tool is mounted at the end portion of the surgical instrument.

The minimal invasive surgery using a surgical robot is performed by introducing the surgical tool of the slave device and the surgical instrument having the surgical tool mounted thereon into the inside of a human body to perform a required operation. In this case, after the surgical tool and the surgical instrument are introduced to the inside of the human body, an inside condition is checked from images collected through an endoscope, one of the surgical tools, and a medical image of the patient obtained before the surgery, for example, a computerized tomography (CT) and a magnetic resonance image (MRI) is used as a supplementary image for reference.

SUMMARY

In some example embodiments, a haptic glove configured to transmit haptic feedback to an operator of a surgical robot system may comprise: a plurality of vibrators on a first surface of the haptic glove, the plurality of vibrators configured to apply vibrations; at least one pressure sensor at a finger part of a second surface of the haptic glove opposite to the first surface, the at least one pressure sensor configured to sense grip force in the finger part; at least one sensation applier on the second surface, the at least one sensation applier configured to apply sensations including vibration or force to the finger part; and/or a controller configured to output the grip force sensed by the at least one pressure sensor, and configured to control the vibrations applied by the plurality of vibrators and the sensations applied by the at least one sensation applier.

In some example embodiments, the plurality of vibrators may be aligned in a longitudinal direction of the finger part, from a fingertip portion to a wrist portion, while being spaced apart from one other at desired intervals.

In some example embodiments, the controller may be configured to determine a vibrator among the plurality of vibrators that is provided in a direction corresponding to a direction of a force applied to a surgical robot of the surgical robot system during surgery, and/or may be configured to control an operating period and an intensity of a vibration of the determined vibrator such that the vibration generated by the determined vibrator corresponds to a magnitude of the applied force.

In some example embodiments, the at least one pressure sensor may be at a fingertip portion of the finger part.

In some example embodiments, the controller may output the grip force sensed by the at least one pressure sensor to a surgical robot of the surgical robot system in real time such that the surgical robot grips a surgical tool with a force corresponding to the grip force.

In some example embodiments, the at least one sensation applier may be at a fingertip portion of the finger part.

In some example embodiments, the at least one pressure sensor and the at least one sensation applier may be at fingertip portions of the finger part corresponding to a thumb and an index finger of the finger part.

In some example embodiments, the controller may be configured to control operation of the at least one sensation applier to generate the sensations including the vibration or the force corresponding to the grip force sensed by a surgical tool of the surgical robot system.

In some example embodiments, the haptic glove may further comprise a rechargeable battery configured to supply power for operating the haptic glove.

In some example embodiments, a surgical robot system may comprise a slave system configured to perform a surgical operation on a patient; and/or a master system configured to control the slave system, the master system including a haptic glove configured to be worn by an operator to control the surgical operation of the slave system. The haptic glove may include a plurality of vibrators on a first surface of the haptic glove, the plurality of vibrators configured to apply vibrations; at least one pressure sensor at a finger part of a second surface of the haptic glove opposite to the first surface, the at least one pressure sensor configured to sense grip force in the finger part; at least one sensation applier on the second surface, the at least one sensation applier configured to apply sensations including vibration or force to the finger part; and/or a controller configured to output the grip force sensed by the at least one pressure sensor to the master system, and further configured to control the vibrations applied by the plurality of vibrators and the sensations applied by the at least one sensation applier according to a control signal of the at least one sensation applier.

In some example embodiments, the slave system may comprise: a surgical tool configured to perform the surgical operation on the patient; a sensor on the surgical tool configured to measure force or torque applied to the surgical tool; an endoscope configured to provide an image of a surgery area inside a body of the patient; and/or a slave controller configured to output a first signal related to the force or torque sensed by the sensor to the master system, and configured to receive a second signal related to the grip force sensed by the at least one pressure sensor of the haptic glove.

In some example embodiments, the master system may comprise: a depth sensor configured to sense position, shape, posture, gesture, or motion of the haptic glove; a display configured to display the image provided by an endoscope of the slave system or a composite image having the image provided by the endoscope overlaid with an image of the haptic glove that is sensed by the depth sensor; and/or a master controller configured to receive a signal sensed by a sensor of the slave system and to control operations of the plurality of vibrators and the at least one sensation applier.

In some example embodiments, the master system may be configured to receive the signal sensed by the sensor of the slave system to determine a vibrator among the plurality of vibrators that is provided in a direction corresponding to a direction of a force applied to a surgical tool, to output a first control signal related to an operating period and an intensity of a vibration of the determined vibrator such that the vibration generated by the determined vibrator corresponds to a magnitude of the applied force, and/or to output a second control signal to control operation of the at least one sensation applier so as to create the sensations including vibration or force corresponding to the grip force sensed by the surgical tool.

In some example embodiments, the master system may further comprise an input configured to turn on/off or temporarily stop the master system controlling the slave system.

In some example embodiments, the input may be embodied in a pedal manipulated by a foot of the operator.

In some example embodiments, a haptic glove configured to transmit haptic feedback to an operator of a surgical robot system may comprise: a plurality of vibrators configured to apply vibrations; at least one pressure sensor at a finger part of the haptic glove configured to sense grip force in the finger part; at least one sensation applier configured to apply sensations including vibration or force to the finger part; and/or a controller configured to output the grip force sensed by the at least one pressure sensor, configured to control the vibrations applied by the plurality of vibrators, and configured to control the sensations applied by the at least one sensation applier.

In some example embodiments, the at least one pressure sensor may be at a fingertip portion of the finger part.

In some example embodiments, the at least one sensation applier may be at a fingertip portion of the finger part.

In some example embodiments, the haptic glove may further comprise a battery configured to supply power for operating the haptic glove.

In some example embodiments, the haptic glove may further comprise a rechargeable battery configured to supply power for operating the haptic glove.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Figure 1:
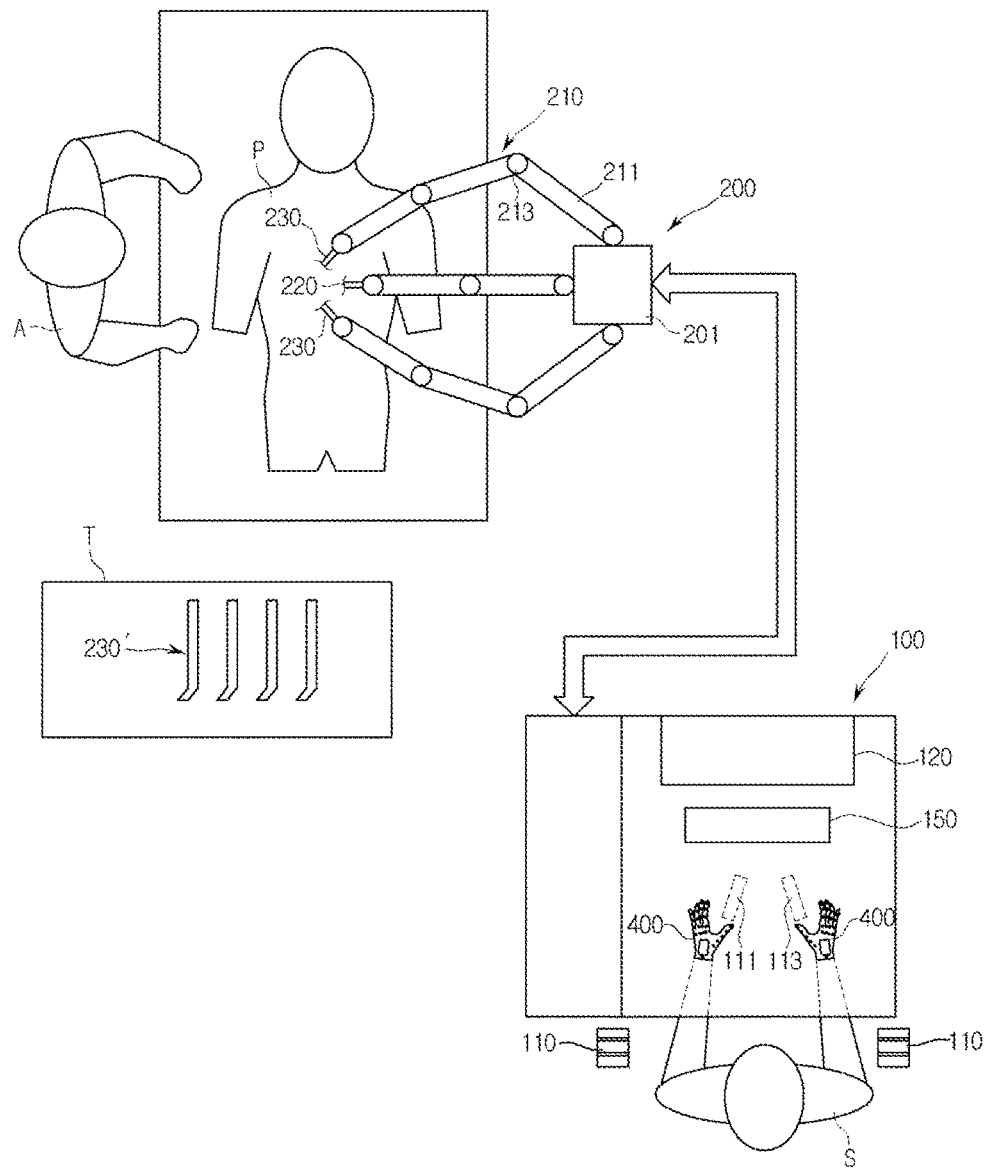
FIG. 1 is a schematic view illustrating a structure of a surgical robot system in accordance with some example embodiments of the present disclosure.

Example embodiments will now be described more fully with reference to the accompanying drawings. Embodiments, however, may be embodied in many different forms and should not be construed as being limited to the embodiments set forth herein. Rather, these example embodiments are provided so that this disclosure will be thorough and complete, and will fully convey the scope to those skilled in the art. In the drawings, the thicknesses of layers and regions may be exaggerated for clarity.

It will be understood that when an element is referred to as being "on," "connected to," "electrically connected to," or "coupled to" to another component, it may be directly on, connected to, electrically connected to, or coupled to the other component or intervening components may be present. In contrast, when a component is referred to as being "directly on," "directly connected to," "directly electrically connected to," or "directly coupled to" another component, there are no intervening components present. As used herein, the term "and/or" includes any and all combinations of one or more of the associated listed items.

It will be understood that although the terms first, second, third, etc., may be used herein to describe various elements, components, regions, layers, and/or sections, these elements, components, regions, layers, and/or sections should not be limited by these terms. These terms are only used to distinguish one element, component, region, layer, and/or section from another element, component, region, layer, and/or section. For example, a first element, component, region, layer, and/or section could be termed a second element, component, region, layer, and/or section without departing from the teachings of example embodiments.

Spatially relative terms, such as "beneath," "below," "lower," "above," "upper," and the like may be used herein for ease of description to describe the relationship of one component and/or feature to another component and/or feature, or other component(s) and/or feature(s), as illustrated in the drawings. It will be understood that the spatially relative terms are intended to encompass different orientations of the device in use or operation in addition to the orientation depicted in the figures.

The terminology used herein is for the purpose of describing particular example embodiments only and is not intended to be limiting of example embodiments. As used herein, the singular forms "a," "an," and "the" are intended to include the plural forms as well, unless the context clearly indicates otherwise. It will be further understood that the terms "comprises," "comprising," "includes," and/or "including," when used in this specification, specify the presence of stated features, integers, steps, operations, elements, and/or components, but do not preclude the presence or addition of one or more other features, integers, steps, operations, elements, components, and/or groups thereof.

Example embodiments may be described herein with reference to cross-sectional illustrations that are schematic illustrations of idealized example embodiments (and intermediate structures). As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle will typically have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature, their shapes are not intended to illustrate the actual shape of a region of a device, and their shapes are not intended to limit the scope of the example embodiments.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and should not be interpreted in an idealized or overly formal sense unless expressly so defined herein.

Reference will now be made to example embodiments, which are illustrated in the accompanying drawings, wherein like reference numerals may refer to like components throughout.

Figure 2:
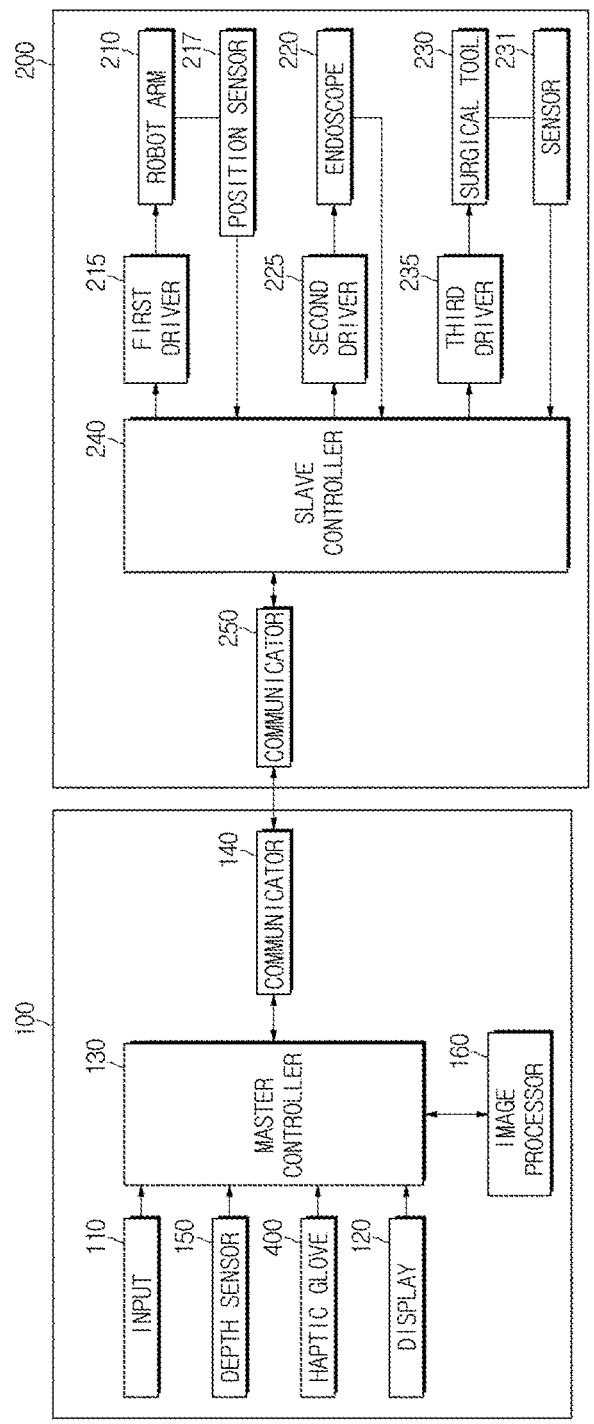
FIG. 2 is a block diagram illustrating the configuration of the surgical robot system in accordance with some example embodiments of the present disclosure.

FIG. 1 is a schematic view illustrating a structure of a surgical robot system in accordance with some example embodiments of the present disclosure. FIG. 2 is a block diagram illustrating the configuration of the surgical robot system in accordance with some example embodiments of the present disclosure.

A surgical robot system may include a slave system 200 that performs a surgery on a patient (P) who lies on an operating table, and a master system 100 that remotely controls the slave system 200 through manipulation by an operator (S), for example, a surgeon. In this case, one or more assistants (A) may be disposed at a side of the patient (P) to assist the operator (S).

Here, the assisting of the operator (S) represents assisting a surgical operation during a surgery, such as replacing a surgical tool 230 that is used, but example embodiments are not limited thereto.

For example, depending on the type of surgical tasks, various surgical tools 230 may be used. Since the number of robot arms 210 of the slave system 200 is limited, the number of surgical tools 230 mounted at one time is also limited. Accordingly, if there is a need to replace the surgical tool 230 during a surgery, the operator (S) instructs the assistant (A) located at a side of the patient (P) to replace the surgical tool 230, and the assistant (A) removes the surgical tool 230, which is not used, from the robot arm 210 of the slave system 200 according to the instruction, and mounts another surgical tool 230', which is placed on a tray (T), on the corresponding robot arm 210.

The master system 100 may be provided as an independent device that is physically separated from the slave system 200, but example embodiments are not limited thereto. For example, the master system 100 may be integrally formed with the slave system 200 into an integrated device.

Referring to FIGS. 1 and 2, the master system 100 may include an input 110 and a display 120.

The input 110 represents a configuration that receives a command to select an operation mode of the surgical robot system, and a command to remotely control an operation of the slave system 200 from the operator (S).

In some example embodiments of the present disclosure, the input 110 includes a clutch pedal into which a manipulation is input to turn on/off or temporarily stop a control of the slave system 200 through the master system 100, and a haptic device into which a manipulation command to control the slave system 200 is input. The input is not limited in particular, and may be composed of a voice recognition device, for example. In addition, in accordance with some example embodiments of the present disclosure, the operator controls the slave system 200 through a haptic glove 400, separately from the input as the above. This will be described later in detail, and the following description will be made in relation to changing a control mode through the clutch pedal and controlling the slave system 200 through the haptic device.

The operator may turn off or temporarily stop the control of the slave system 200 through the master system 100 by stepping on the clutch pedal during manipulation of the master system 100 by a desired number of times (that may or may not be predetermined) or at a desired intensity (that may or may not be predetermined). In addition, if the clutch pedal is stepped on by a desired number of times (that may or may not be predetermined) or at a desired intensity (that may or may not be predetermined) in a state in which the control is finished or temporarily stopped, the control of the slave system 200 through the master system 100 may be turned on again.

Since the operator commonly manipulates the master system 100 by use of hands, the changing of the control mode may be achieved by manipulating the clutch pedal using feet that are relatively free.

The haptic device is illustrated as including two handles 111 and 113 as an example in FIG. 1, but example embodiments are not limited thereto. For example, the haptic device may include one handle or three or more handles.

Referring to FIG. 1, the operator (S) may control the operation of the robot arm 210 of the slave system 200 by manipulating the two handles 111 and 113 using both hands, respectively, to control the operation of the robot arm 210 of the slave system 200. Although not shown in FIG. 1 in detail, each of the handles 111 and 113 may include an end effector, a plurality of links 211, and a plurality of joints 213.

The end effector represents a portion that comes into direct contact with the hands of the operator (S), and may be provided in the form of a pencil and a stick, but the shape of the end effector is not limited thereto.

The joint 213 represents a portion connected between the links 211, and may have 1 degree of freedom or a higher degree of freedom. Degree of freedom (DOF) represents a degree of freedom in Kinematics or Inverse Kinematics. The degree of freedom of a mechanism represents the number of independent motions of a mechanism or the number of parameters that determine an independent motion of a relative position between links 211. For example, in a three-dimensional space composed of x-axis, y-axis, and z-axis, an object has at least of three degrees of freedom to determine a spatial position of the object (the position in each axis) and three degrees of freedom to determine a spatial posture of the object (the rotation angle in each axis). In detail, in a case in which an object may be movable along each axis, and rotatably on each axis, the object may be understood as having six degrees of freedom.

In addition, each joint 213 is provided with a detector (not shown) to detect state information that represents the state of the joint 213, for example, force/torque information applied to the joint 213, and position and speed information of the joint 213. Accordingly, as the operator (S) manipulates the haptic device, the detector (not shown) may detect state information of the input 110 that is manipulated, and a master controller 130 generates a control signal corresponding to the state information of the input 110 detected by the detector (not shown), and transmits the generated control signal to the slave system 200 through a communicator 140. That is, the master controller 130 of the master system 100 may generate a control signal according to the manipulation of the input 110 by the operator (S), and transmit the generated control signal to the slave system 200 through the communicator 140.

The haptic glove 400 is a glove that can be wearable on hands of the operator. As the operator moves the hands while wearing the haptic glove 400, a depth sensor 150 recognizes the shape, position, posture, gesture, and motion of the haptic glove 400, to display an image displayed on the display 120 combined with a representation of the haptic glove 400 in an overlay manner.

The operator may control the operation of the surgical tool 230 of the slave system 200 by moving hands while observing the image of the haptic glove 400 that is overlaid on the image displayed on the display 120. In order to describe such a control of the surgical tool 230 in detail, an image displayed on the display 120 will be described first.

The display 120 of the master system 100 may display an actual image of the inside of the body of the patient (P) collected through the endoscope 220 and a three-dimensional image of a medical image obtained before the patient has a surgery. To this end, the master system 100 may include an image processor 160 that receives image data transmitted from the slave system 200 and outputs the image data to the display 120. Here, the "image data" may include an actual image collected through the endoscope 220, and a three-dimensional image generated from a medical image taken before the patient has a surgery, but example embodiments are not limited thereto.

The image processor 160 converts the medical image obtained before the patient has a surgery into a three-dimensional image, and projects the three-dimensional image onto an actual image collected through the endoscope 220 from the slave system 200, thereby generating a virtual image. The image processor 160 may store the three-dimensional image of the medial image obtained before the patient has a surgery, and a virtual image having the three-dimensional image projected onto an image collected through the endoscope 220. Here, "the medical image obtained before the surgery" includes a computed tomography (CT) image, a magnetic resonance imaging (MRI) image, a position emission tomography (PET) image, a single photon emission computed tomography (SPECT) image, and/or an ultrasonography (US) image, but example embodiments are not limited thereto.

In detail, the image processor 160 receives a medical image from a medial image database constructed based on medical images obtained before a surgery, for example, a CT image or an MRI image for each patient, converts the received medical image into a three-dimensional image, and stores the converted three-dimensional image. In addition, the image processor 160 receives an actual image of a surgery area of inside the patient that is collected through the endoscope 220 from the slave system 200, generates a virtual image having the three-dimensional image projected onto the actual image, and stores the generated virtual image.

Figure 4:
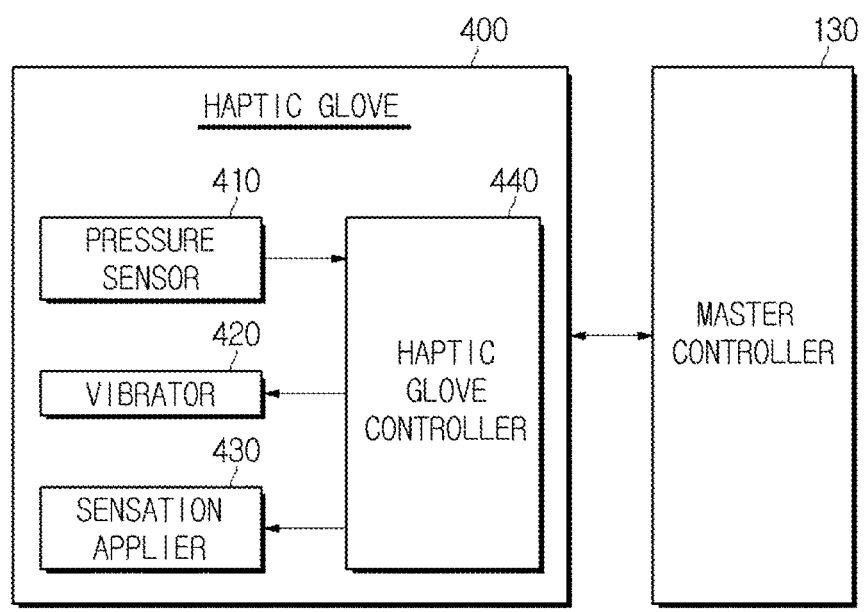
FIG. 4 is a block diagram illustrating the configuration of a haptic glove.

In addition, the image processor 160 receives information about a current position of the surgical tool 230 from the slave system 200, and creates an image of a virtual surgical tool at a matching region in the virtual image. Here, the "position information" represents coordinates, and the image processor 160 may create an image of the virtual surgical tool at coordinates matched to the received coordinates of the surgical tool 230 in the virtual image. If the actual surgical tool 230 is imaged (e.g., videoed, photographed, etc.) through the endoscope 220 as shown in FIG. 4, a portion on which the virtual surgical tool overlaps the actual surgical tool 230 may represent the actual surgical tool 230.

Figure 3:
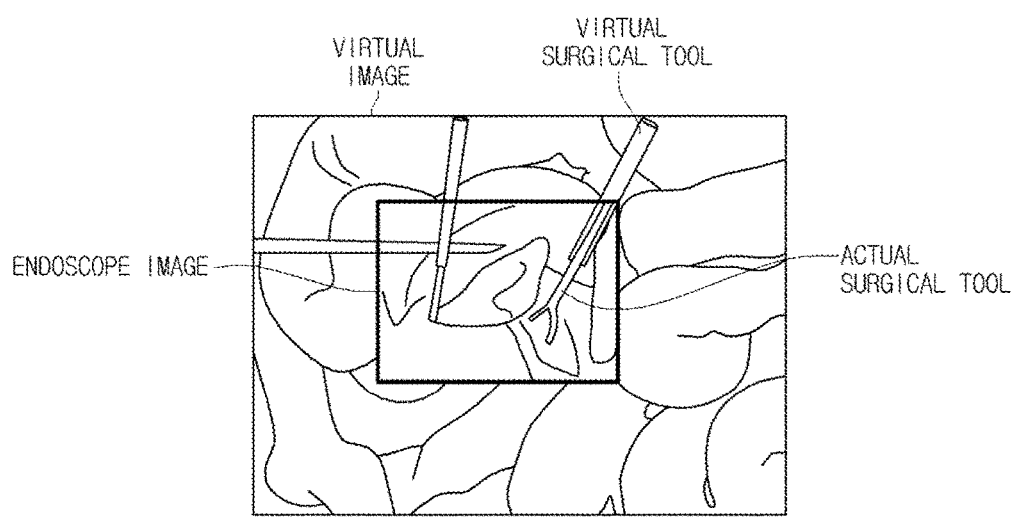
FIG. 3 is a drawing illustrating an image having an image of a surgery area obtained through an endoscope and a virtual image on which an actual surgical tool and a virtual surgical tool are created.

FIG. 3 is a drawing illustrating an image having an image of a surgery area obtained through an endoscope and a virtual image on which an actual surgical tool 230 and a virtual surgical tool are created.

That is, the virtual image in accordance with some example embodiments may be a combined image including a three-dimensional image of a medical image obtained before a surgery of the patient (P), an endoscope image obtained through the endoscope 220, and a virtual surgical tool created using position information of the surgical tool 230 received from the slave system 200. In this case, if the image obtained through the endoscope 220 does not include the actual surgical tool 230, only the virtual surgical tool is combined into an augmented reality image, and if the image obtained through the endoscope 220 includes the actual surgical tool 230, the actual surgical tool 230 is combined to be connected to the virtual surgical tool.

As described above, the three-dimensional image and the virtual image that are generated and stored by the image processor 160 are displayed on the display 120, and are transmitted to the slave system 200 and other display device through the communicator 140.

The display 120 of the master system 100 displays the virtual image generated by the image processor 160.

The display 120 may be composed of one or more monitors, and each monitor is embodied to individually display required information for a surgery.

For example, if the display 120 is composed of three monitors, one of the three monitors may display the actual image collected through the endoscope 220 and the three dimension image generated using the medical image obtained before the patient has a surgery, and remaining two monitors may display information about an operation state of the slave system 200 and patient information, respectively. In this case, the number of monitors may vary depending the type and variety of information that is desired to be displayed.

Here, the "patient information" is information representing the state of a patient, for example, biomedical information, such as the temperature, pulsation, respiration, and blood pressure. In order to provide such biomedical information to the master system 100, the slave system 200, which will be described later, may further include a temperature measurement module, a pulsation measurement module, a respiration measurement module, and a blood pressure measurement module. To this end, the master system 100 may further include a signal processor (not shown) that receives biomedical information transmitted from the slave system 200, processes the received biomedical information, and outputs the processed biomedical information to the display 120.

As the operator starts controlling the slave system 200 while wearing the haptic glove 400, the display 120 displays an image having the virtual image generated by the image processor 160 combined with an image of the haptic glove 400 in an overlay manner. As the operator moves hands while wearing the haptic glove 400, the depth sensor 150 recognizes the shape, position, posture, gesture, and motion of the haptic glove 400 to calculate data, and outputs the calculated data to the image processor 160. The image processor 160, based on the data output from the depth sensor 150, combines an image of the haptic glove 400 to be overlaid on the virtual image displayed on the display 120 and displays the combined image.

As the operator takes a synchronizing motion by moving the hands such that the image of the haptic glove 400 is located on the position of the surgical tool 230 in the virtual image being displayed on the display 120 while observing the display 120, and matching the shape of the hand to correspond to the shape of the surgical tool 230, the master system 100 notifies that the motion of the haptic glove 400 is synchronized with the motion of the surgical tool 230. As the motion of the haptic glove 400 is synchronized with the motion of the surgical tool 230, the operator may control the motion of the surgical tool 230 while observing the display 120.

In order to add the impression that the operator performs a surgery while holding the actual surgical tool 230, in addition to the synchronization of the motion of the haptic glove 400 with the motion of the surgical tool 230 using the depth sensor 150, a vibrator 420 and a sensation applier 430 of the haptic glove 400 feedbacks a sensation, such as a force or a torque, that is applied to the surgical tool 230 during a surgery to the operator. This will be described in detail, after the slave system 200 is described.

The slave system 200 may include a plurality of robot arms 210 and various surgical tools 230 mounted on end portions of the robot arms 210. The plurality of robot arms 210 may be fixedly coupled to a body 201 and supported by the body 201. In this case, the number of surgical tools 230 and the robot arms 210 that are used at one time may be determined depending on a diagnosis method, a surgery method, and a spatial limitation of a surgery room.

In addition, each of the plurality of robot arms 210 may include a plurality of links 211 and a plurality of joints 213, and each joint 213 connects the links 211 to each other, and may have 1 degree of freedom or more.

In addition, a first driver 215 may be provided on each of the joints 213 of the robot arms 210 to control the motion of the robot arm 210 according to a control signal transmitted from the master system 100. For example, the operator (S) manipulates the input 110 of the master system 100, the master system 100 generates a control signal corresponding to state information of the input 110 that is manipulated, and transmits the generated control signal to the slave system 200. A slave controller 240 drives the first driver 215 according to the control signal transmitted from the master system 100, thereby controlling the motion of each joint 213 of the robot arm 210. Meanwhile, each joint 213 of the robot arm 210 of the slave system 200 is embodied to be moved according to the control signal transmitted from the master system 100, but may be embodied to move according to an external force. That is, the assistant (A) located adjacent to the operating table may manually move each joint 213 of the robot arm 210, thereby controlling the position of the robot arm 210.

Although not shown in FIG. 1, each of the surgical tools 230 may include a housing mounted at an end portion of the robot arm 210, and a shaft extending from the housing by a desired length (that may or may not be predetermined).

A driving wheel may be coupled to the housing, and the driving wheel may be connected to the surgical tools 230 through wires, so that the surgical tools 230 may be operated in a desired manner according to rotation of the driving wheel. To this end, the robot arm 210 may be provided at the end portion thereof with a third driver 235 to rotate the driving wheel. For example, as the operator (S) manipulates the input 110 of the master system 100, the master system 100 generates a control signal corresponding to state information of the input 110, and transmits the generated control signal to the slave system 200. The slave controller 240 drives the third driver 235 according to the control signal transmitted from the master system 100, thereby operating the third driver 235 and thus operating the surgical tools 230 in a desired manner. However, the mechanism that operates the surgical tools 230 is not limited thereto, and various electrical/mechanical mechanisms may be employed to implement a required operation of the surgical tools 230 for a robot surgery.

Various surgical tools 230 may include a skin holder, a suction line, a scalpel, scissors, graspers, a medical needle, a needle holder, a staple applier, and a cutting blade, but example embodiments are not limited thereto. The surgical tools 230 may be any other tool that is required for a surgery.

In general, the surgical tool 230 may be broadly divided into a main surgical tool and a subsidiary surgical tool. Here, the "main surgical tool" may represent a tool that performs a direct surgical operation, such as an incision, a suture, a congelation, and a cleansing of a surgery area (for example, a scalpel, and a medical needle), and the "subsidiary surgical tool" may represent a tool that assists the operation of the main surgical tool other than performing a direct surgical operation on the surgery area (for example, a skin holder).

The endoscope 220 does not perform a direct surgical operation on the surgery area, but is used as a tool that assists the operation of the main surgical tool, and thus in a broad sense, the endoscope 220 may be regarded as a subsidiary surgical tool. As the endoscope 220, a laparoscope, a thoracoscope, an arthroscope, a nasal speculum, a cystoscope, a gastroscope, a rectoscope, and a cardioscope may be used.

In addition, as the endoscope 220, a complementary metal-oxide semiconductor (CMOS) camera and a charge coupled device (CCD) camera may be used, but example embodiments are not limited thereto. In addition, the endoscope 220 may include a lighting member to radiate light onto the surgery area. In addition, the endoscope 220, as shown in FIG. 12, may be mounted at the end portion of the robot arm 210, and the slave system 200 may further include a second driver 225 to operate the endoscope 220. In addition, the slave controller 240 may transmit an image collected through the endoscope 220 to the master system 100 through a communicator 250.

In addition, the slave system 200 in accordance with some example embodiments of the present disclosure may further include a position sensor 217 to detect the current positions of the surgical tools 230 as show in FIG. 2. In this case, as the position sensor 217, a potentiometer and an encoder may be used, but example embodiments are not limited thereto.

The position sensor 217 may be provided at respective joints 213 of the robot arms 210 on which the surgical tools 230 are mounted, and the position sensor 217 may detect information about a motion state of each joint 213 of the robot arm 210, and the slave controller 240 may calculate current positions of the surgical tools 230 by receiving the detected information from the position sensor 217. In this case, the slave controller 240 may calculate the current positions of the surgical tools 230 by applying the input information to the kinematics of the robot arms. Herein, the calculated current position may be coordinates. In addition, the slave controller 240 may transmit the calculated coordinates of the position of the surgical tool 230 to the image processor 160 of the master system 100 that is described above.

In this manner, since the current positions of the surgical tools 230 are estimated by detecting the states of the respective joints 213 of the robot arms 210 on which the surgical tools 230 are mounted, the positions of the surgical tools 230 are easily estimated even in a case in which the surgical tools 230 are located outside of a view of the endoscope 220 or are blocked by internal organs within the view of the endoscope 220.

In addition, a sensor 231 may be installed at the end portion of the surgical tool 230 to sense an external force including a force or a torque applied to the surgical tool 230. As the sensor 231, a force/torque sensor may be used.

As the sensor 231, a strain gauge may be used, and the sensor 231 available for use is not limited thereto. The sensor may be embodied using other types of general sensors that can measure the external force including a force or a torque.

The strain gauge is a sensor that measures a deformation of an object that takes place due to an external force, and is attached to the object to measure the deformation and the degree of deformation. For example, the strain gauge may be formed by processing a resistance line in the form of a grid on a thin electrical insulation material that serves as a base, or processing a resistance film on the base through a photo etching process, attaching an extending line to the resistance line or the resistance film, so as to utilize the characteristic that the resistance is changed with the change of the length of the metal.

In detail, if a tension is applied to the strain gauge, the length of the resistance line formed on the base is increased, and the resistance increases in proportion to the increased length. On the other hand, a stress is applied to the strain gauge, the length of the resistance line formed on the base is decreased, and the resistance is reduced in proportion to the decrease length. In this manner, the generated resistance is measured and calculated so that the deformation of the object and the magnitude of an external force applied to the object may be calculated.

The sensor 231, when sensing an external force applied to the surgical tool 230, outputs the sensed external force to the slave controller 240, and the slave controller 240 transmits the sensed external force to the master controller 130. The master controller 130 generates a control signal that operates the vibrator 420 and the sensation applier 430 of the haptic glove 400 such that the operator who wears the haptic glove 400 senses a force or torque corresponding to the external force, by analyzing the external force, applied to the surgical tool 230, which is transmitted from the slave system 200.

Figure 5A:
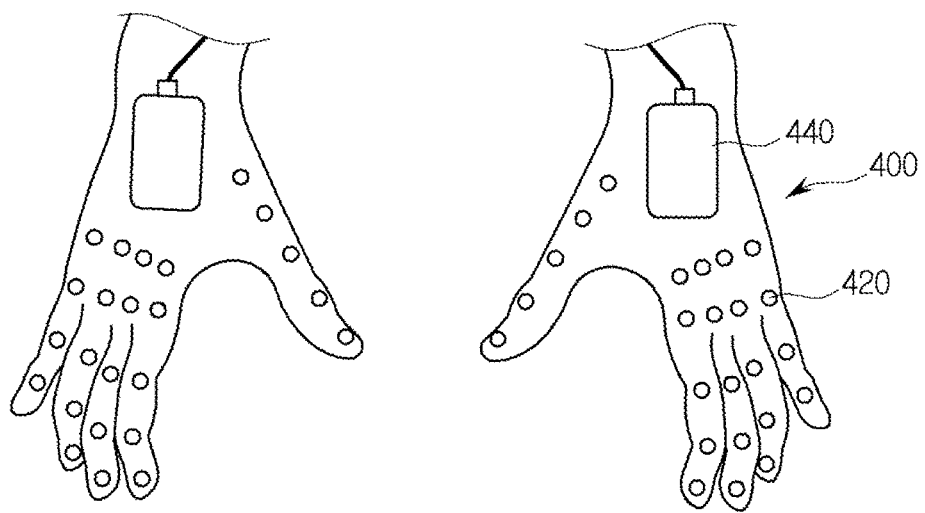
FIGS. 5A to 5C are conceptual views illustrating a haptic glove on which a pressure sensor and a sensation applier are installed.
Figure 5B:
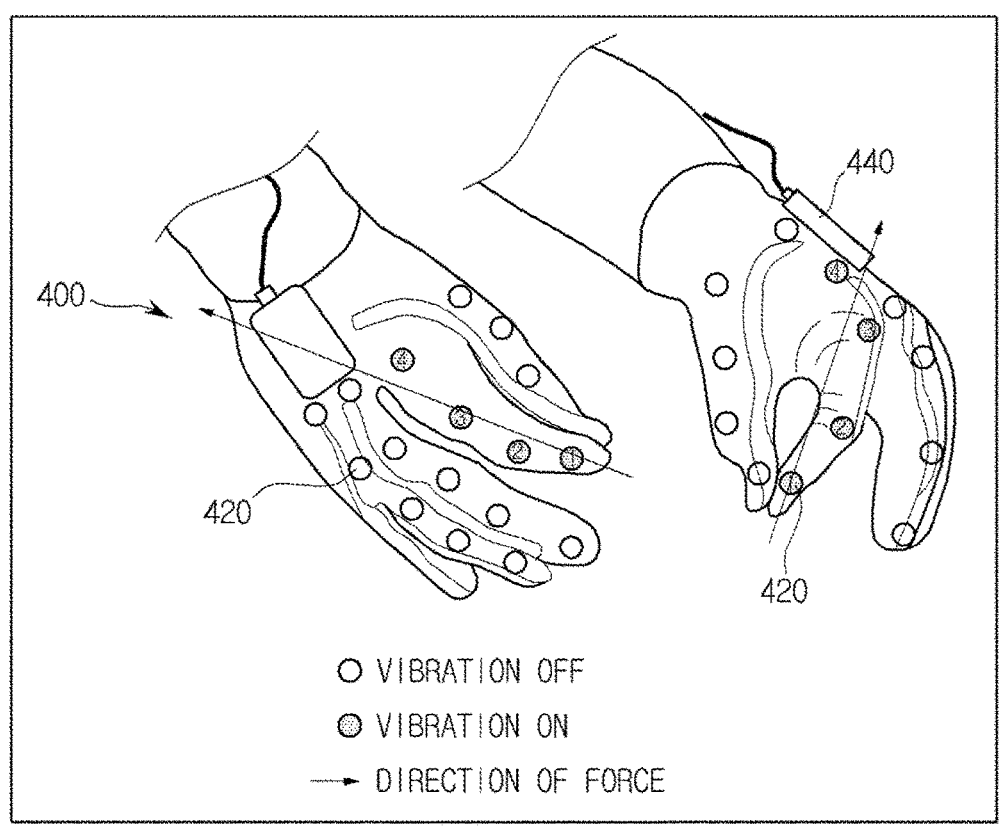
Figure 5C:
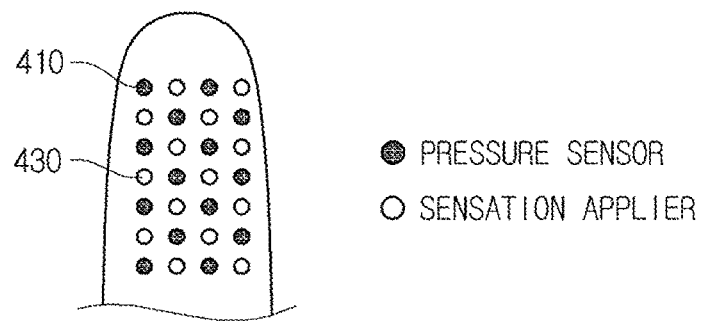

FIG. 4 is a block diagram illustrating the configuration of a haptic glove, and FIGS. 5A to 5C are conceptual views illustrating the haptic glove 400 having a pressure sensor 410 and the sensation applier 430 installed thereon.

Referring to FIG. 4, the haptic glove 400 includes a glove forming a body of the haptic glove 400, and the vibrator 420, the pressure sensor 410, the sensation applier 430 and a controller 440 of the haptic glove 400 that are installed on the glove.

Referring to FIG. 5A, the vibrator 420 may be provided in a plurality thereof that are attached to one surface of the haptic glove 400. The plurality of vibrators 420 may be aligned in a longitudinal direction of a finger part from a tip of the finger part to a wrist part while being spaced apart from one other by a desired interval (that may or may not be predetermined). The attachment position of the vibrator 420 is only an example, and the vibrator 420 may be attached in a different position and a different rule. As the vibrator 420, a tactor may be used.

The controller 440 of the haptic glove 400 may be provided at a back of the hand of the haptic glove 400 to operate the vibrator 420 and the sensation applier 430 by receiving a control signal that operates the vibrator 420 and the sensation applier 430 from the master controller 130. The controller 440 of the haptic glove 400 and the master controller 130 may transmit data with the master controller 130 in a wired/wireless communication scheme. Although the controller 440 of the haptic glove 400 in FIG. 5A is illustrated as being connected to the master controller 130 in a wired scheme, the controller 440 of the haptic glove 400 may transmit and receive data in a wireless communication scheme.

In addition, a rechargeable battery may be installed on a desired region (that may or may not be predetermined), in which the controller 440 is provided. Accordingly, the controller 440 may transmit data without a wired connection in a state that the battery is charged.

Referring to FIG. 5B, if the sensor 231 installed on the surgical tool 230 of the slave system 200 senses an external force applied to the surgical tool 230, the master controller 130 receives the external force, and generates a control signal to operate the vibrator 420 and the sensation applier 430 such that the operator can feel a sensation corresponding to the external force.

For example, the master controller 130 determines a vibrator 420 provided along a direction corresponding to a direction of the external force applied to the surgical tool 230 among the vibrators 420 installed on the haptic glove 400, and determines the intensity of vibration of the determined vibrator 420 such that the vibration generated from the determined vibrator 420 corresponds to the magnitude of the external force. In order that the operator feels the direction of the external force, the vibration period of the vibrator 420 also may be determined to sequentially operate the vibrators 420, arranged along the direction of the external force, from one provided at the tip of the finger up to one provided at the back of the hand.

Referring to FIG. 5B, as for the vibrators 420, a direction corresponding to a direction of an external force applied to the surgical tool 230 is illustrated, and the vibrator 420 determined to be installed in the direction is illustrated to be operate. The vibrator 420 in operation is indicated in a dark color.

In order that the operator feels the direction of the external force, the vibrators 420 arranged along the direction of the external force may be sequentially operated starting from one ① provided at the tip of the finger to one ④ provided at the back of the hand.

Referring to FIG. 5C, the pressure sensor 410 and the sensation applier 430 are installed on a surface of a finger part opposite to the surface on which the vibrator 420 is installed.

The pressure sensor 410 is provided to sense a grip force GF acting between fingers when the operator takes an action such as gripping a virtual object with fingers. Accordingly, the pressure sensor 410 is installed at a surface opposite to the surface on which the vibrator 420 is installed as shown in FIG. 5C.

The grip force GF sensed by the pressure sensor 410 is transmitted to the third driver 235 that operates the surgical tool 230 of the slave system 200, and the third driver 235 operates the surgical tool 230 such that the surgical tool 230 takes an action, such as gripping an internal tissue of a human body, with a force corresponding to the grip force GF.

A reaction force is applied to the surgical tool 230 when the surgical tool 230 takes an action, such as gripping an internal tissue of the human, based on the grip force GF of the operator, and the sensation applier 430 configured to apply a sensation, including a force or a vibration, to transmit the reaction force to the finger part from which the grip force GF is generated is installed on the same area as the pressure sensor 410. That is, as the sensor 231 installed on the surgical tool 230 senses a reaction force against the gripping operation of the surgical tool 230 and transmits the reaction force to the master controller 130, and the master controller 130 outputs a control signal such that the sensation applier 430 applies a sensation including a force or a vibration corresponding to the reaction force.

The sensation applier 430 does not simply apply a vibration as in the vibrator 420. For example, the sensation applier 430 may apply a pressing force in addition to a vibration, thereby enabling the operator to feel a sensation as if the operator directly uses the surgical tool 230. The pressing force is included in examples of the sensation, and a sensation such as temperature or pain may be applied. The sensation applier 430 may be embodied as a tactile display to transmit the sensation to fingers of the operator.

The pressure sensor 410 and the sensation applier 430 may be mainly installed on an end link of the finger part as shown in FIG. 5C, and in particular, on the thumb finger and the index finger of the finger part. Alternatively, the pressure sensor 410 and the sensation applier 430 may be installed on other fingers and other links of the finger part. In addition, although the pressure sensor 410 is separately provided from the sensation applier 430 in FIG. 5C, example embodiments are not limited thereto, and the pressure sensor 410 and the sensation applier 430 may be integrally formed with each other, and installed.

Although the control signal to operate the vibrator 420 and the sensation applier 430 of the haptic glove 400 is generated by the master controller 130 in the above description, example embodiments are not limited thereto. For example, the control signal may be generated by the controller 440 of the haptic glove 400.

Figure 6:
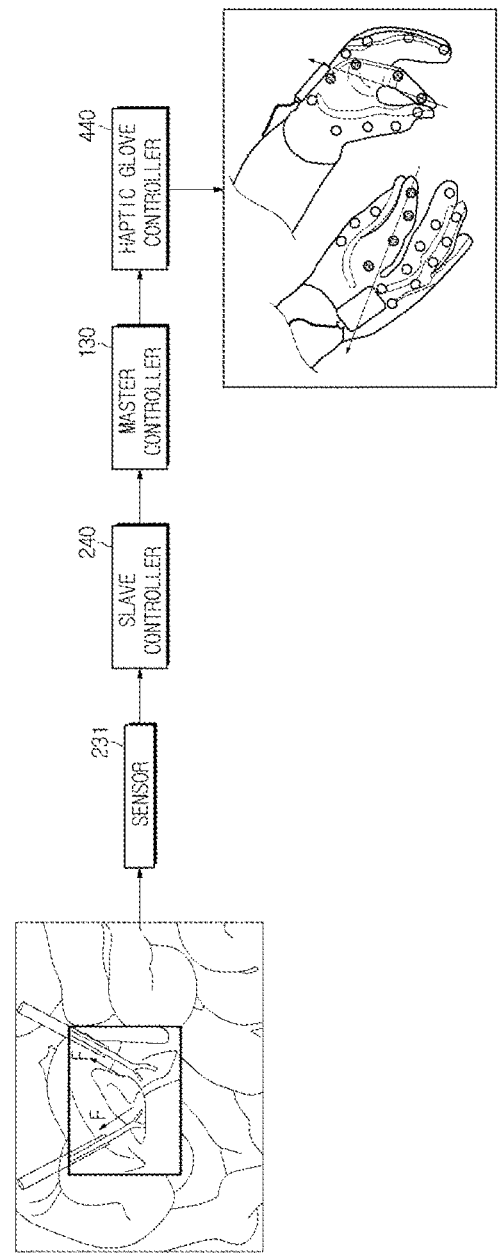
FIG. 6 is a drawing showing a process of transmitting a force sensed by the surgical tool to the haptic glove.
Figure 7:
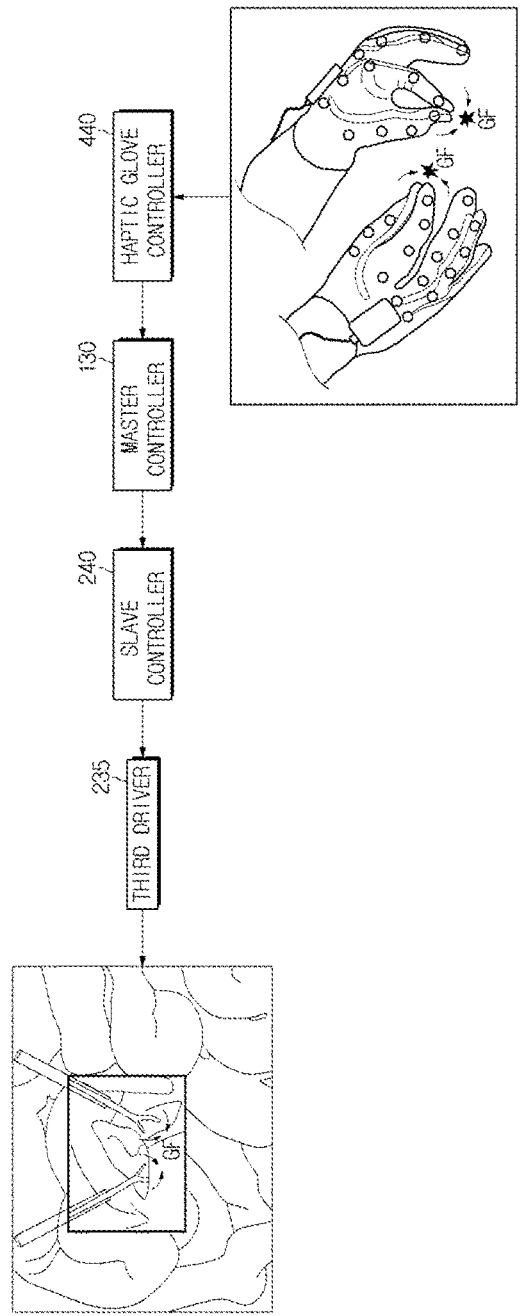
FIG. 7 is a drawing showing a process of transmitting a force sensed by the haptic glove to the surgical tool.

FIG. 6 is a drawing showing a process of transmitting a force sensed by the surgical tool to the haptic glove 400, and FIG. 7 is a drawing showing a process of transmitting a force sensed by the haptic glove 400 to the surgical tool 230.

Referring to FIG. 6, the sensor 231 installed on the surgical tool 230 of the slave system 200 senses an external force applied to the surgical tool 230. The sensor 231 senses the magnitude and direction of the external force, converts the sensed magnitude and direction to data, and outputs the converted data to the slave controller 240.

The slave controller 240 transmits the data output from the sensor 231 to the communicator 140 of the master system 100 through a communicator 250. As the communicator 140 of the master system 100 receives the data, the master controller 130 generates a control signal to operate the vibrator 420 such that the operator feels a sensation corresponding to the external force, and outputs the generated control signal to the controller 440 of the haptic glove 400. The controller 440 of the haptic glove 400 operates the vibrator 420 according to the control signal output from the master controller 130.

For example, the master controller 130 determines a vibrator 420 provided along a direction corresponding to a direction of the external force applied to the surgical tool 230 among the vibrators 420 installed on the haptic glove 400, and determines the magnitude of vibration of the determined vibrator 420 such that the vibration generated from the determined vibrator 420 corresponds to the magnitude of the external force. In order for the operator to feel the direction of the external force, the vibration period of the vibrator 420 also may be determined to sequentially operate the vibrators 420, arranged along the direction of the external force, from one provided at the tip of the finger to one provided at the back of the hand.

In addition, the sensor 231 installed on the surgical tool 230 of the slave system 200 senses a reaction force against the gripping operation of the surgical tool 230, converts the reaction force into data, and outputs the data to the slave controller 240.

The slave controller 240 transmits the data output from the sensor 231 to the communicator 140 of the master system 100 through a communicator 250. As the communicator 140 of the master system 100 receives the data, the master controller 130 generates a control signal to operate the sensation applier 430 such that the operator feels a sensation including a force or a vibration corresponding to the reaction force, and outputs the generated control signal to the controller 440 of the haptic glove 400. The sensation applier 430 generates a sensation according to the control signal output from the controller 440 of the haptic glove 400.

The sensation applier 430 does not simply apply a vibration as in the vibrator 420. For example, the sensation applier 430 applies a pressing force in addition to a vibration, thereby enabling the operator to feel a sensation as if the operator directly uses the surgical tool 230. The pressing force is included in examples of the sensation, and a sensation such as temperature or pain may be applied. The sensation applier 430 may be embodied as a tactile display to transmit the sensation to fingers of the operator.

Referring to FIG. 7, as the pressure sensor 410 of the haptic glove 400 senses a grip force GF in between the fingers, the pressure sensor 410 converts the sensed grip force GF into data, and outputs the data to the controller 440 of the haptic glove 400, and the controller 440 of the haptic glove 400 outputs the data to the master controller 130.

The master controller 130 transmits grip force GF related data to the slave system 200 through a communicator 250. As the communicator 250 of the slave system 200 receives the grip force GF data, and the slave controller 240 outputs a control signal to drive the third driver 235 such that the surgical tool 230 takes an action, such as gripping an internal tissue of the human body, with a force corresponding to the grip force GF.

The third driver 235 operates the surgical tool 230 such that the surgical tool 230 grips the tissue with a force corresponding to the grip force GF of the operator according to the control signal.

A reaction force generated due to the operation of the surgical tool 230 is retransmitted to the haptic glove 400 through the process shown in FIG. 6.

It should be understood that the exemplary embodiments described therein should be considered in a descriptive sense only and not for purposes of limitation. Descriptions of features or aspects within each embodiment should typically be considered as available for other similar features or aspects in other embodiments.

What is claimed is:

1. A haptic glove configured to transmit haptic feedback to an operator of a surgical robot system, the haptic glove comprising:
    a plurality of vibrators on a first surface of the haptic glove, the plurality of vibrators configured to apply vibrations;
    at least one pressure sensor at a finger part of a second surface of the haptic glove opposite to the first surface, the at least one pressure sensor configured to sense grip force acting between fingers in the finger part;
    at least one sensation applier on the second surface, the at least one sensation applier configured to apply sensations including vibration or force to the finger part; and
    a controller configured to output the grip force sensed by the at least one pressure sensor, and configured to control the vibrations applied by the plurality of vibrators and the sensations applied by the at least one sensation applier,
    wherein the controller is configured to determine at least two of the plurality of vibrators of the haptic glove that are arranged on a finger along a direction corresponding to a direction of a force applied to a surgical robot of the surgical robot system during surgery among the plurality of vibrators, and is configured to control an intensity of a vibration of the determined vibrators such that the vibration generated by the determined vibrators corresponds to a magnitude of the applied force, and is configured to control an operating period of the vibration generated by the determined vibrators such that the determined vibrators sequentially operate along a direction of the finger corresponding to the direction of the applied force.

2. The haptic glove of claim 1, wherein the plurality of vibrators are aligned in a longitudinal direction of the finger part, from a fingertip portion to a wrist portion, while being spaced apart from one another at desired intervals.

3. The haptic glove of claim 1, wherein the at least one pressure sensor is at a fingertip portion of the finger part.

4. The haptic glove of claim 1, wherein the controller outputs the grip force sensed by the at least one pressure sensor to the surgical robot of the surgical robot system in real time such that the surgical robot grips a surgical tool with a force corresponding to the grip force.

5. The haptic glove of claim 1, wherein the at least one sensation applier is at a fingertip portion of the finger part.

6. The haptic glove of claim 1, wherein the at least one pressure sensor and the at least one sensation applier are at fingertip portions of the finger part corresponding to a thumb and an index finger of the finger part.

7. The haptic glove of claim 1, wherein the controller is configured to control operation of the at least one sensation applier to generate the sensations including the vibration or the force corresponding to the grip force sensed by a surgical tool of the surgical robot system.

8. The haptic glove of claim 1, further comprising:
    a rechargeable battery configured to supply power for operating the haptic glove.

9. A surgical robot system, comprising:
    a slave system configured to perform a surgical operation on a patient; and
    a master system configured to control the slave system, the master system including a haptic glove configured to be worn by an operator to control the surgical operation of the slave system;
    wherein the haptic glove includes,
        a plurality of vibrators on a first surface of the haptic glove, the plurality of vibrators configured to apply vibrations;
        at least one pressure sensor at a finger part of a second surface of the haptic glove opposite to the first surface, the at least one pressure sensor configured to sense grip force acting between fingers in the finger part;
        at least one sensation applier on the second surface, the at least one sensation applier configured to apply sensations including vibration or force to the finger part; and
        a controller configured to output the grip force sensed by the at least one pressure sensor to the master system, and further configured to control the vibrations applied by the plurality of vibrators and the sensations applied by the at least one sensation applier according to a control signal of the at least one sensation applier,
    wherein the master system is configured to receive the signal sensed by a sensor of the slave system to determine at least two of the plurality of vibrators of the haptic glove that are arranged on a finger along a direction corresponding to a direction of a force applied to a surgical tool among the plurality of vibrators, to output a first control signal to control an intensity of a vibration of the determined vibrators such that the vibration generated by the determined vibrators corresponds to a magnitude of the applied force and to control an operating period of the vibration generated by the determined vibrators such that the determined vibrators sequentially operate along a direction of the finger corresponding to the direction of the applied force.

10. The surgical robot system of claim 9, wherein the slave system comprises:
    the surgical tool configured to perform the surgical operation on the patient;
    the sensor on the surgical tool configured to measure force or torque applied to the surgical tool;
    an endoscope configured to provide an image of a surgery area inside a body of the patient; and
    a slave controller configured to output a first signal related to the force or torque sensed by the sensor to the master system, and configured to receive a second signal related to the grip force sensed by the at least one pressure sensor of the haptic glove.

11. The surgical robot system of claim 9, wherein the master system comprises:
    a depth sensor configured to sense position, shape, posture, gesture, or motion of the haptic glove;

a display configured to display an image provided by an endoscope of the slave system or a composite image having the image provided by the endoscope overlaid with an image of the haptic glove that is sensed by the depth sensor; and a master controller configured to receive a signal sensed by a sensor of the slave system and to control operations of the plurality of vibrators and the at least one sensation applier.

12. The surgical robot system of claim 11, wherein the master system further comprises an input configured to turn on/off or temporarily stop the master system controlling the slave system.

13. The surgical robot system of claim 12, wherein the input is embodied in a pedal configured to be manipulated by a foot of the operator.

14. The surgical robot system of claim 9, wherein the master system is configured to output a second control signal to control operation of the at least one sensation applier so as to create the sensations including vibration or force corresponding to the grip force sensed by the surgical tool.

15. A haptic glove configured to transmit haptic feedback to an operator of a surgical robot system, the haptic glove comprising:

a plurality of vibrators configured to apply vibrations;

at least one pressure sensor at a finger part of the haptic glove configured to sense grip force acting between fingers in the finger part;

at least one sensation applier configured to apply sensations including vibration or force to the finger part; and a controller configured to output the grip force sensed by the at least one pressure sensor, configured to control the vibrations applied by the plurality of vibrators, and configured to control the sensations applied by the at least one sensation applier, wherein the controller is configured to determine at least two of the plurality of vibrators of the haptic glove that are provided on a finger in a direction corresponding to a direction of a force applied to a surgical robot of the surgical robot system during surgery among the plurality of vibrators, and is configured to control an intensity of a vibration of the determined vibrators such that the vibration generated by the determined vibrators corresponds to a magnitude of the applied force, and is configured to control an operating period of the vibration generated by the determined vibrators such that the determined vibrators sequentially operate along a direction of the finger corresponding to the direction of the applied force.

16. The haptic glove of claim 15, wherein the at least one pressure sensor is at a fingertip portion of the finger part.

17. The haptic glove of claim 15, wherein the at least one sensation applier is at a fingertip portion of the finger part.

18. The haptic glove of claim 15, further comprising:
a battery configured to supply power for operating the haptic glove.

19. The haptic glove of claim 15, further comprising:
a rechargeable battery configured to supply power for operating the haptic glove.

* * * * *